US00PP26180P2

(12) United States Plant Patent
Zampini

(10) Patent No.: US PP26,180 P2
(45) Date of Patent: Dec. 1, 2015

(54) ***PHILADELPHUS* PLANT NAMED 'INCSNOZAM'**

(50) Latin Name: *Philadelphus coronarius*
Varietal Denomination: Incsnozam

(71) Applicant: LCN Holdings, Inc., Perry, OH (US)

(72) Inventor: James W. Zampini, Madison, OH (US)

(73) Assignee: LAKE COUNTRY NURSERY, Perry, OH (US)

( * ) Notice: Subject to any disclaimer, the term of this patent is extended or adjusted under 35 U.S.C. 154(b) by 85 days.

(21) Appl. No.: 13/986,354

(22) Filed: Apr. 23, 2013

Related U.S. Application Data

(60) Provisional application No. 61/687,386, filed on Apr. 24, 2012.

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Keith O. Robinson

(74) *Attorney, Agent, or Firm* — Penny J. Aguirre

(57) ABSTRACT

A new cultivar of *Philadelphus coronaria,* 'Incsnozam', characterized by its foliage that is green in spring and summer and turns a golden yellow in fall, its upright, mounded plant habit, and its double white, fragrant flowers.

2 Drawing Sheets

Botanical classification: *Philadelphus coronarius.*
Variety denomination: 'Incsnozam'.

CROSS REFERENCE TO RELATED APPLICATIONS

This application is co-pending with U.S. Plant Patent applications filed for cultivars derived from the same breeding program entitled *Philadelphus* Plant Named 'Icezam' (U.S. patent application Ser. No. 13/986,355) and *Philadelphus* Plant Named 'Romanizam' (U.S. patent application Ser. No. 13/986,353).

BACKGROUND OF THE INVENTION

The present invention relates to a new and distinct cultivar of *Philadelphus coronarius* and will be referred to hereafter by its cultivar name, 'Incsnozam'. 'Incsnozam' is a new cultivar of mock orange, a shrub grown for use as an ornamental landscape plant.

The new cultivar of *Philadelphus* was discovered as a naturally occurring whole plant mutation by the Inventor in Perry, Ohio in summer of 1997. The new cultivar was discovered growing in a seed bed that had been planted with seed derived from unnamed plants of *Philadelphus coronaria*. The exact parent plants are unknown.

Asexual reproduction of the new cultivar was first accomplished by the Inventor using softwood stem cuttings in summer of 2008 in Perry, Ohio. The characteristics of this cultivar have been determined to be stable and are reproduced true to type in successive generations.

SUMMARY OF THE INVENTION

The following traits have been repeatedly observed and represent the characteristics of the new cultivar as grown outdoors in Perry, Ohio. These attributes in combination distinguish 'Incsnozam' as a unique cultivar of *Philadelphus.*

1. 'Incsnozam' exhibits foliage that is green in spring and summer and turns a golden yellow in fall.
2. 'Incsnozam' exhibits, double white, fragrant flowers.
3. 'Incsnozam' exhibits an upright, mounded plant habit.

Typical plants of the *Philadelphus coronarius* differ from 'Incsnozam' in having single flowers and in lacking golden foliage in fall. 'Incsnozam' can be compared to the cultivars; 'Icezam' and 'Romanizam' selected by the same Inventor. 'Icezam' differs from 'Incsnozam' in having smaller single flowers that are less fragrant and in having variegated foliage that lacks golden yellow fall color. 'Romanizam' differs from 'Incsnozam' in having flowers that are larger, semi-double and more fragrant and in having foliage that lacks golden yellow fall color. 'Incsnozam' can also be compared to the cultivar *Philadelphus×virginalis* 'Minnesota Snowflake' (not patented). 'Minnesota Snowflake' is similar to 'Incsnozam' in having double white flowers, however 'Minnesota Snowflake' differs in having flower petals that are more narrow and lanceolate in shape.

BRIEF DESCRIPTION OF THE DRAWINGS

The accompanying colored photographs illustrate the overall appearance and distinct characteristics of the new *Philadelphus*. The photographs were taken of a two year-old plant as grown outdoors in trial garden in Perry, Ohio.

The photograph in FIG. 1 provides an overall view of the growth habit of 'Incsnozam'.

Figure 1:
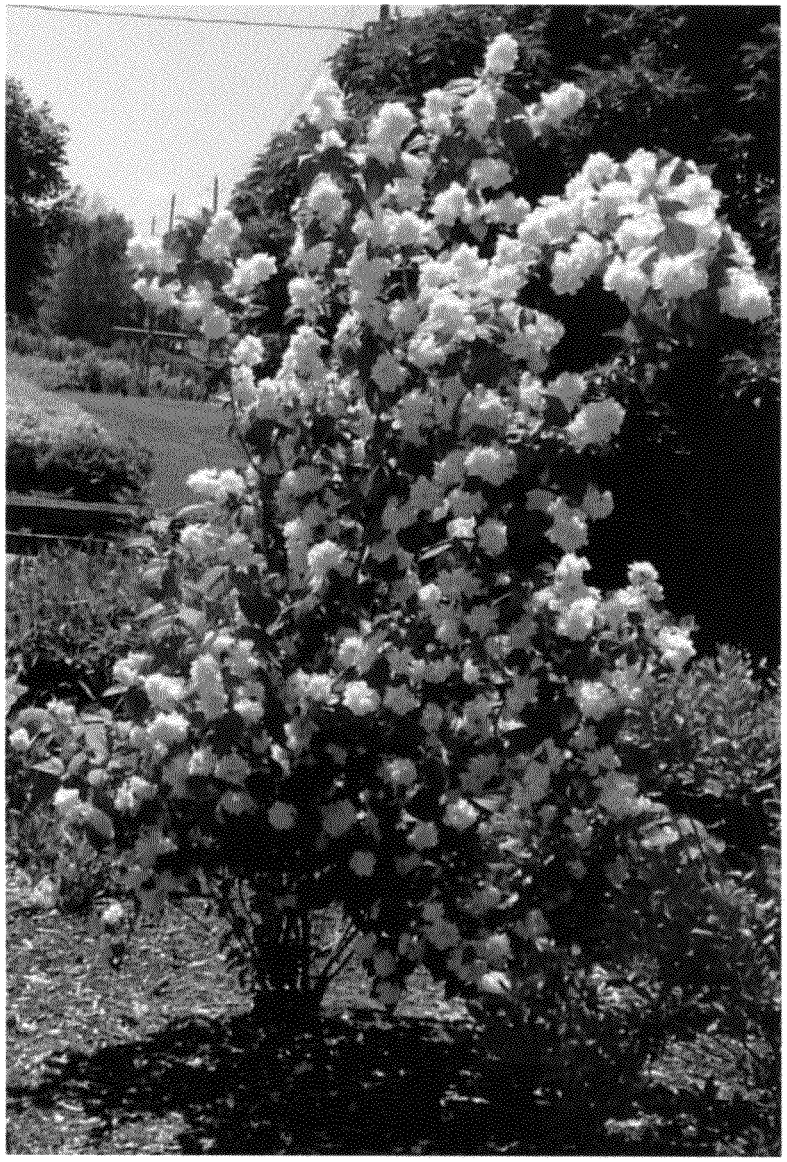
Figure 2:
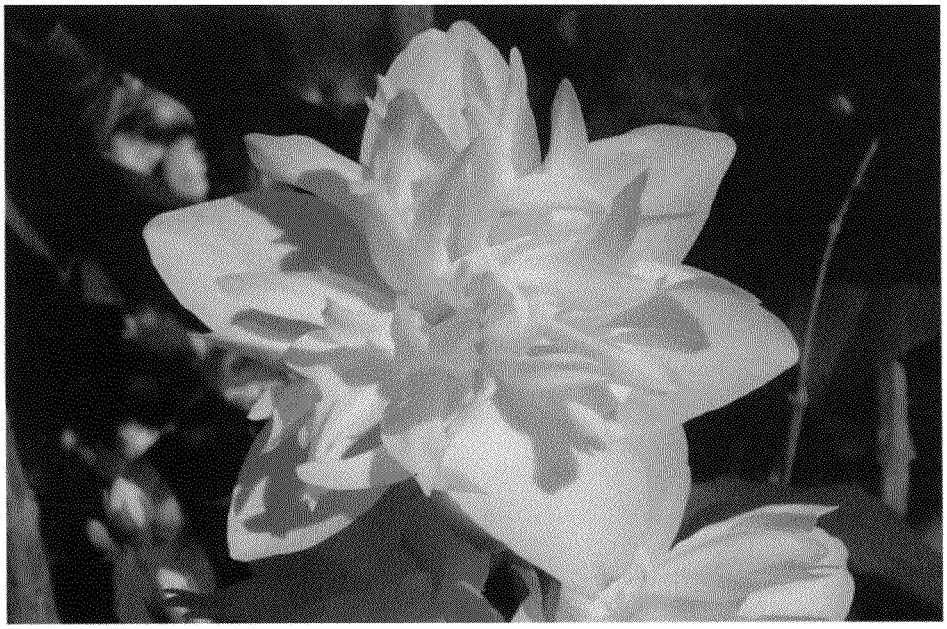

The photograph in FIG. 2 provides a close-up view of the flowers of 'Incsnozam'.

Figure 3:
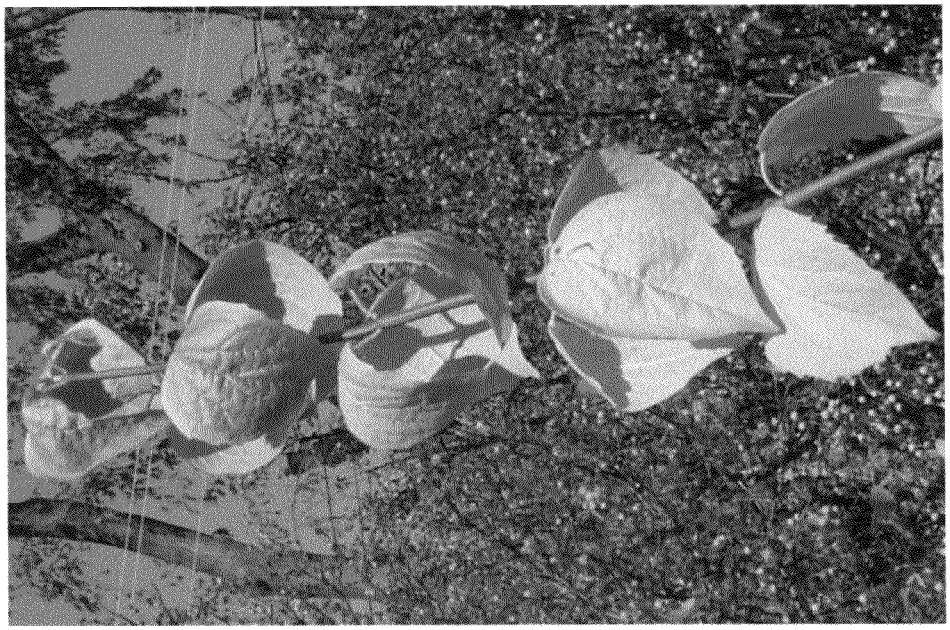

The photograph in FIG. 3 provides a close-up view of the fall foliage of 'Incsnozam'.

The colors in the photograph may differ slightly from the color values cited in the detailed botanical description, which accurately describe the colors of the new *Philadelphus.*

DETAILED BOTANICAL DESCRIPTION

The following is a detailed description of 2 year-old plants of the new cultivar as grown outdoors in full sun in a trial plot in Perry, Ohio. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms for about 4 weeks in late May to early June in Ohio.

*Plant type.*—Deciduous shrub.

*Plant habit.*—Upright and mounded.

*Plant size.*—Reaches about 2.4 to 2.5 m (8 to 10 feet) in height 1.8 to 2.4 m (6 to 8 feet) in width in three years in the landscape.

*Cold hardiness.*—At least to U.S.D.A. Zones 4.

*Diseases and pests.*—No susceptibility or resistance to diseases or pests has been observed.

*Root description.*—Fibrous, moderately dense.

*Propagation.*—Softwood stem cuttings.

*Growth rate.*—Vigorous.

*Root development.*—Roots initiate in about 2 weeks, rooted cuttings fully develop in a 2.5 inch container in about 60 days.

Stem description:

*Shape.*—Oval.

*Stem color.*—New growth; N144A, mature wood; a blend of 156A and 177D and 199A.

*Stem size.*—Basal branches; an average of 1 m in length and 8 mm in diameter, lateral branches; an average of 14 cm in length and 2 mm in diameter.

*Stem surface.*—New growth; glabrous and densely covered in soft wooly hairs up to 1.5 mm in length and 157C in color, mature wood; slightly exfoliating (shreddy).

*Stem aspect.*—Upright to slightly outward at an average angle of 20° to upright.

*Branching.*—Average of 6 main branches, and an average of 8 lateral branches per main stem, branch internode length; an average of 3 cm.

Foliage description:

*Leaf shape.*—Ovate.

*Leaf division.*—Simple.

*Leaf base.*—Acute.

*Leaf apex.*—Acuminate.

*Leaf fragrance.*—None.

*Leaf venation.*—Primarily pinnate, color matches leaf coloration on upper and lower surface.

*Leaf margins.*—Serrated.

*Leaf arrangement.*—Opposite.

*Leaf attachment.*—Petiolate.

*Leaf surface.*—Upper surface matte, lower surface slightly glossy, upper surface very sparsely covered with very short hairs 0.5 mm in length and matches leaf color.

*Leaf internode length.*—An average of 4 mm.

*Leaf size.*—An average of 4.5 cm in length and 3 cm in width.

*Leaf quantity.*—An average of 8 per stem.

*Leaf color.*—Newly expanded leaves upper surface; center a blend of 144A and 146A, random spotting of 138C, outside edges 160D, newly expanded leaves lower surface; center 146A, outside edges 160D, mature leaves upper surface; center a blend of 144A and 146A, random spotting of 138C, 160C mature leaves lower surface; center 146A, outside edges 160C, fall color on upper and lower surface; a blend of 7A and 1A.

*Petioles.*—About 5 mm in length and 1 mm in width, color N144A, matte surface covered with sparse hairs matching surface color.

*Stipules.*—None.

Inflorescence description:

*Inflorescence type.*—Most typically is short racemes of about 7 double flowers, occasionally in pairs or single.

*Inflorescence size.*—Raceme is an average of 5 cm in diameter and 8 cm in depth.

*Flower buds.*—Globose in shape, an average of 1 cm in depth and 8 mm in diameter, NN155B in color with sepal portion matching sepal color.

*Flower fragrance.*—Fragrant, orange scented.

*Lastingness of flowers.*—About 10 days.

*Flower aspect.*—Outward to upright.

*Flower quantity.*—An average of 4 per lateral stem, an average of 15 per main stem.

*Flower type.*—Rotate.

*Flower size.*—Average of 5 cm in diameter and 1.25 cm in depth.

*Peduncles.*—Average of 8 cm in length and 2 mm in diameter, color N144A, glabrous surface, oval in shape.

*Pedicels.*—None, sessile to peduncle.

*Calyx.*—Rotate in shape, an average of 8 mm in depth and 2 cm in width.

*Sepals.*—4, ovate in shape, acute apex, cuneate base, entire margin, an average of 8 mm in length and 2.5 cm in width, color on upper surface when opening and mature 137B, color on lower surface when opening and mature 137C, upper surface is pubescent and lower surfaces is glabrous.

*Petals.*—4, un-fused, ovate in shape, margin entire, apex acute and occasionally notched, an average of 2.5 cm in length and 1.25 cm in width, outer and inner surface is glabrous, color of inner surface when opening and mature; NN155B, color of outer surface when opening and mature; NN155B.

*Petaloids.*—An average of 20, un-fused, lanceolate in shape, margin entire, apex acute to acuminate, an average of 1.5 cm in length and 8 mm in width, outer and inner surface is glabrous, color of inner surface when opening and mature; NN155B, color of outer surface when opening and mature; NN155B.

Reproductive organs:

*Gynoecium.*—4 pistil, united, about 1 cm in length, style is an average of 9 mm in length, and 155A in color, stigma is 161D in color, ovary is inferior and surrounded by nectar secreting disk; 151D in color, 7 mm in diameter and 3 mm in length.

*Androcoecium.*—About 4 stamens, filaments are 155A in color and an average of 1 cm in length, anthers are 160B in color, an average of 2 mm in length, basifixed and oblong in shape, pollen is low in quantity and 4D in color.

*Fruit and seed.*—Fruit; 4-valved capsule, about 7 mm in length and width, dries to 199B in color, seed: none observed.

It is claimed:

1. A new and distinct cultivar of *Philadelphus* plant named 'Incsnozam' as herein illustrated and described.

* * * * *